(12) United States Patent
Arts et al.

(10) Patent No.: US 6,342,622 B1
(45) Date of Patent: Jan. 29, 2002

(54) INDENYL COMPOUNDS FOR THE POLYMERIZATION OF OLEFINS

(75) Inventors: Henricus J. Arts, Munstergeleen; Mirko Kranenburg, Maastricht; Ramon H. A. M. Meijers, Brunssum; Edwin G. Ijpeij, Sittard; Gerardus J. M. Gruter, Maastricht; Felix H. Beijer, Sittard, all of (NL)

(73) Assignee: DSM B.V., Heerlen (NL)

( * ) Notice: Subject to any disclaimer, the term of this patent is extended or adjusted under 35 U.S.C. 154(b) by 0 days.

(21) Appl. No.: 09/591,689

(22) Filed: Jun. 12, 2000

Related U.S. Application Data

(60) Provisional application No. 60/162,892, filed on Nov. 1, 1999.

Foreign Application Priority Data

Jun. 11, 1999 (EP) .............................................. 99201856

(51) Int. Cl.⁷ ............................ C07F 17/00; C08F 4/44; B01J 31/00
(52) U.S. Cl. ............................... 556/53; 556/1; 556/43; 556/58; 502/103; 502/117; 502/120; 534/15; 526/160; 526/351; 526/352; 526/943
(58) Field of Search ............................... 556/1, 43, 53, 556/58; 534/15; 502/103, 117, 120; 526/160, 943, 351, 352

(56) References Cited

U.S. PATENT DOCUMENTS

| | | | |
|---|---|---|---|
| 5,646,322 A | 7/1997 | Van Beek et al. | ............. 556/11 |
| 5,948,873 A | * 9/1999 | Santi et al. | .................. 526/129 |
| 6,232,484 B1 | * 5/2001 | Schaverien et al. | ............ 556/53 |

OTHER PUBLICATIONS

Ellis et al., Organometallics, vol. 12, No. 11, pp. 4391–4401 (1993).*

* cited by examiner

*Primary Examiner*—Porfirio Nazario-Gonzalez
(74) *Attorney, Agent, or Firm*—Pillsbury Winthrop LLP

(57) ABSTRACT

Indenyl compound of formula (1)

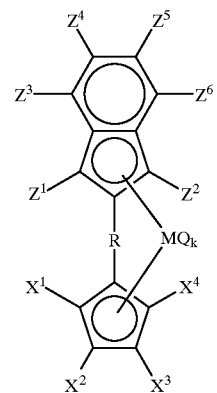

wherein:
M is a transition metal from the lanthanides or from group 3, 4, 5 or 6 of the Periodic System of Elements,
Q is an anionic ligand to M,
k is the number of Q groups,
R is a bridging group
and Z and X are substituents, wherein R contains at least one sp2-hybridized carbon atom that is bonded to the indenyl group at the 2-position with the exclusion of Ti(deshydronorbiphenacene) dichloride.

24 Claims, No Drawings

INDENYL COMPOUNDS FOR THE POLYMERIZATION OF OLEFINS

This application claims the benefit of U.S. Provisional Application No. 60/162,892, filed Nov. 1, 1999.

The invention relates to indenyl compounds that can be used as catalyst component for the polymerisation of olefins. The invention also relates to a process for the polymerisation of olefins, using indenyl compounds. Such indenyl compounds are for instance known from WO-A-94/11406.

In said patent publication indenyl compounds are described of formula

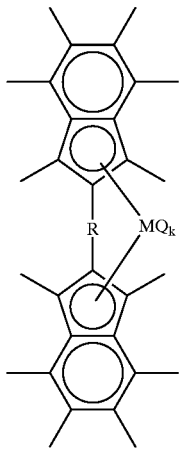

wherein:
M is a transition metal from the lanthanides or from group 3, 4, 5 or 6 of the Periodic System of Elements,
Q is an anionic ligand to M,
k is the number of Q-groups and equals the valence of M minus 2, and
R is a bridging group. It is now surprisingly discovered that indenyl compounds, wherein R contains at least one sp2-hybridised carbon atom that is bonded to the indenyl group at the 2-position, are more active and/or give polymers with a higher molecular weight (Mw) and/or yield a polypropylene with a low amount of misinsertions when used as a catalyst component during the polymerisation of olefins.

The indenyl compounds according to the invention are indenyl compounds according to (1)

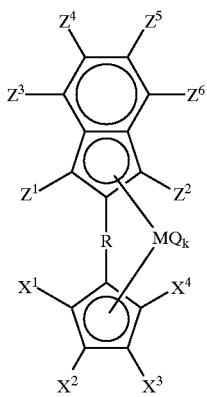

wherein:
M is a transition metal from the lanthanides or from group 3, 4, 5 or 6 of the Periodic System of Elements,
Q is an anionic ligand to M,
k is the number of Q groups, and equals the valence of M minus 2,
R is a bridging group containing at least one sp2-hybridised carbon atom that is bonded to the indenyl group at the 2-position,
and Z and X are substituents, with the exclusion of Ti(deshydronorbiphenacene)dichloride. In 'Synthesis, Structure, and Properties of Chiral Titanium and Zirconium Complexes Bearing Biaryl Strapped Substituted Cyclopentadienyl Ligands', W. W. Ellis c.s., Organometallics 1993, 12, 4391–4401 Ti(deshydronorbiphenacene)dichloride is described, but not the polymerisation of olefins with this indenyl compound.

The various components of the indenyl compound of the present invention will hereafter be discussed in more detail.

a) The Transition Metal M

The transition metal M is selected from the lanthanides or from group 3, 4, 5 or 6 of the Periodic System of Elements. The Periodic System of Elements is understood to be the new IUPAC version as printed on the inside cover of the Handbook of Chemistry and Physics, 70th edition, CRC Press, 1989–1990. The transition metal M is preferably chosen from the group Ti, Zr, Hf, V and Sm. Most preferably the transition metal M is Ti, Zr or Hf.

b) The Anionic Ligand Q

The Q group in the indenyl compounds according to the invention comprises one or more uni- or polyvalent anionic ligands to the transition metal M. As examples of such ligands, which may be the same or different, the following can be mentioned:

a hydrogen atom, a halogen atom, an alkyl group, an aryl group, an aralkyl group, an alkoxy group, an aryloxy group, a group with a heteroatom chosen from group 14, 15 or 16 of the Periodic System of Elements, such as:

an amine group or amide group, a sulfur-containing compound, such as sulphide and sulphite, a phosphorus-containing compound, such as phosphine and phosphite.

The ligand Q can also be a monoanionic ligand bonded to the transition metal M via a covalent metal-carbon bond and which is additionally capable to non-covalently interact with M via one or more functional groups. The functional group mentioned above can be one atom, but also a group of atoms connected together. The functional group is preferably an atom of group 17 of the Periodic Table of the Elements or a group containing one or more elements from groups 15, 16 or 17 of the Periodic Table of the Elements. Examples of functional groups are F, Cl, Br, dialkylamino and alkoxy groups. Q can for instance be a phenyl group in which at least one of the ortho-positions is substituted with a functional group capable of donating electron density to the transition metal M. Q can also be a methyl group in which one or more of the alpha-positions is substituted with a functional group capable of donating electron density to the transition metal M. Examples of methyl groups substituted in one or more of the alpha-positions are benzyl, diphenylmethyl, ethyl, propyl and butyl substituted with a functional group capable of donating electron density to the transition metal M. Preferably at least one of the ortho-positions of a benzyl-group is substituted with a functional group capable of donating electron density to the transition metal M.

Examples of these Q groups are: 2,6-difluorophenyl, 2,4,6-trifluorophenyl, pentafluorophenyl, 2-alkoxyphenyl, 2,6-dialkoxyphenyl, 2,4,6-tri(trifluoromethyl)phenyl, 2,6-di(trifluoromethyl)phenyl, 2-trifluoromethylphenyl, 2-(dialkylamino)benzyl and 2,6-(dialkylamino)phenyl. The man skilled in the art can determine the suitability of these and other ligands through simple experimenting.

The number of Q groups in the indenyl compound according to the invention (index k in formula (1)) is determined by the valence of the transition metal M and the valence of the Q groups itself. In the indenyl compounds according to the invention k is equal to the valence of M minus 2 divided by the valence of Q.

Preferably, Q is a mono-anionic ligand. Most preferably, Q is Cl or a methyl group.

c) The Bridging Group R

R is a bridging group containing at least one sp2-hybridised carbon atom that is bonded to the indenyl group at the 2-position. In general and in this description, the substituent locants of the indenyl ring are numbered in accordance with the IUPAC Nomenclature of Organic Chemistry, 1979, rule A 21.1. The numbering of the substituents for indene is given below. This numbering is analogous in the case of an indenyl ligand:

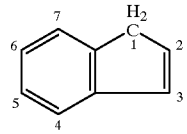

The R group connects the indenyl group with the cyclopentadienyl group in the indenyl compound according to the invention. Sp2-hybridised carbon atoms are also known as trigonal carbon atoms. The chemistry related to sp2-hybridised carbon atoms is for instance descibed by S.N. Ege, Organic Chemistry, D.C. Heath and Co., 1984, p. 51–54. Sp2-hybridised carbon atoms are carbon atoms that are connected to three other atoms. In the indenyl compounds according to the invention the sp2-hybridised carbon atom is in any case connected to the indenyl group at the 2-position.

The sp2-hybridised carbon atom may be a part of, for instance, an alkylene-containing bridging group R or of an aryl group forming part of the bridging group R.

Alkylene-containing bridging groups can be, for instance of the formulas

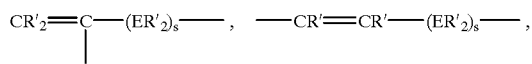

wherein R' is a hydrogen atom, a halogen atom, an alkyl group, an aryl group, an aralkyl group, an alkoxy group, an aryloxy group, a group with a heteroatom chosen from group 14, 15 or 16 of the Periodic System of Elements, such as
- an amine group or amide group,
- a sulfur-containing compound, such as sulphide and sulphite,
- a phosphorus-containing compound, such as phosphine and phosphite, E can be carbon, silica or germanium atom and
s is 1–20.

Examples of alkylene-containing bridging groups are ethylene, propylene, which can also be subsituted.

Examples of aryl groups that can form part of a bridging group are phenylene, biphenylene, pyridyl, furyl, thiophyl and N-substituted pyrroles, such as N-phenylpyrrole or an inorganic compound containing an aromatic group, for instance a metallocene compound and a ferrocene compound.

The bridging group R preferably contains at least one aryl group; preferably the aryl group is a phenylene group. When R is a phenylene group the indenyl compounds are more active catalyst components. More preferably R is a bisaryl group; preferably a 2,2'-biphenylene. When R is a 2,2'-biphenylene group the indenyl compound, as a catalyst component, gives rise to better comonomer incorporation, polymers with a higher molecular weight and to a propylene homopolymer with a higher isotacticity when propylene is polymerised.

d) The Substituents $X_1$–$X_4$

The cyclopentadienyl group may be substituted. The substituents X may each separately be hydrogen or a hydrocarbon radical with 1–20 carbon atoms (e.g. alkyl, aryl, aryl alkyl). Examples of alkyl groups are methyl, ethyl, propyl, butyl, hexyl and decyl. Examples of aryl groups are phenyl, mesityl, tolyl and cumenyl, Examples of aryl alkyl groups are benzyl, pentamethylbenzyl, xylyl, styryl and trityl. Examples of other substituents are halides, such as chloride, bromide, fluoride and iodide, methoxy, ethoxy and phenoxy. Also, two adjacent hydrocarbon radicals may be connected with each other in a ring system. In this way an indenyl can be formed by connection of $X_1$ and $X_2$, $X_2$ and $X_3$, $X_3$ and $X_4$, or fluorenyl can be formed by connection of both $X_1$ and $X_2$ and $X_3$ and $X_4$.

X may also be a substituent which instead of or in addition to carbon and/or hydrogen may comprise one or more heteroatoms from group 14, 15 or 16 of the Periodic System of Elements. Examples of such a heteroatom containing substituents are: alkylsulphides (like MeS-, PhS-, n-butyl-S-), amines (like $Me_2N$-, n-butyl-N-), Si or B containing groups (like $Me_3Si$- or $Et_2B$-) or P-containing groups (like $Me_2P$- or $Ph_2P$-).

e) The Substituents $Z_{1–Z6}$

The indenyl group may be substituted. The substituents Z may each separately be a substituent as described under d for X. Two adjacent hydrocarbon radicals may be connected with each other in a ring system. The $Z_1$ and $Z_2$ substituents can together with the $X_1$ and $X_4$ substituents form a second bridge that connects the indenyl group with the cyclopentadienyl group in the indenyl compound according to the invention. The second bridge can be a bridge as described under c, but can also be a bridge having the following structure:

$$(-ER^3{}_2-)_p$$

where p=1–4 and E is an element from group 14 of the Periodic System. R3 can be the same substituent as described for X under d.

Preferably, because these indenyl compounds are the most active ones, the indenyl compound has the structure of formula (2)

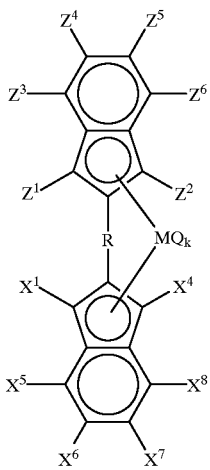

wherein:
M is a transition metal from the lanthanides or from group 3, 4, 5 or 6 of the Periodic System of Elements,
Q is an anionic ligand to M,
k is the number of Q groups, and equals the valence of M minus 2,
R is a bridging group containing at least one sp2-hybridised carbon atom that is bonded to one of the indenyl groups at the 2-position,
and Z and X are substituents as defined herein before.

The invention is also directed to ligand presursors that can be used to prepare the indenyl compounds according to the invention. The ligand precursors have a structure according to formula (3)

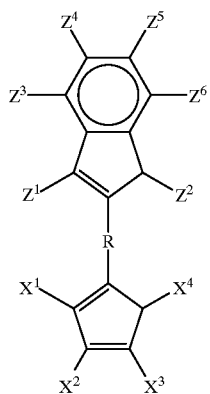

wherein:
R is a bridging group containing at least one sp2-hybridised carbon atom that is bonded to the indene group at the 2-position
and Z and X are substituents as defined here before, with the exclusion of
2,2'-bis(2-1H-indenyl)-6,6'-dimethyl-1,1'-biphenyl,
2,2'-bis(2-1H-indenyl)-1,1'-biphenyl and
2,2'-bis(2-1H-indenyl)-1,1'-binaphthalene.

The meaning of the various components is further described hereabove.

In 'Synthesis, Structure, and Properties of Chiral Titanium and Zirconium Complexes Bearing Biaryl Strapped Substituted Cyclopentadienyl Ligands', W. W. Ellis c.s., Organometallics 1993, 12, 4391–4401 the ligand precursors 2,2'-bis(2-1H-indenyl)-6,6'-dimethyl-1,1'-biphenyl, 2,2'-bis(2-1H-indenyl)-1,1'-biphenyl and 2,2'-bis(2-1H-indenyl)-1,1'-binaphthalene are mentioned. In this article the use of indenyl compounds according to the invention for the polymerisation of olefins is not described and the advantages of the indenyl compounds according to the invention are not suggested.

Preferably the ligand precursors have a structure according to formula (4)

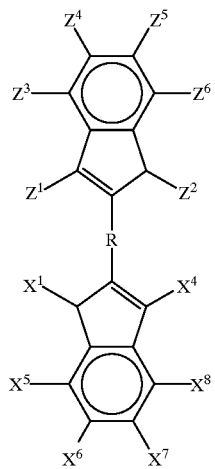

wherein:
R is a bridging group containing at least one sp2-hybridised carbon atom that is bonded to one of the indene groups at the 2-position
and Z and X are substituents as defined herein before with the exclusion of
2,2'-bis(2-1H-indenyl)-6,6'-dimethyl-1,1'-biphenyl,
2,2'-bis(2-1H-indenyl)-1,1'-biphenyl and
2,2'-bis(2-1H-indenyl)-1,1'-binaphthalene. More preferably the bridge R contains at least one phenylene group. Most preferably the bridge R is a 2,2'-biphenylene with the exclusion of a ligand with the structure 2,2'-bis(2-1H-indenyl)-1,1'-biphenyl.

The invention further relates to a process for the preparation of ligand precursors of formula (3) by a cross-coupling reaction of two 2-indenyl precursors of formula (5) with a bridging precursor $R(Y^2)_2$ (5)

wherein:
$X^1$ to $X^8$: are substituents,
$Y^1$ and $Y^2$ are either a leaving group or a metal containing group,
R is a bridging group,
comprising the steps of reacting 2 equivalents of the 2-indenyl precursors with 1 equivalent of the bridging precursor, $Y^2$ being a leaving group in the case that $Y^3$ is a metal containing group and $Y^2$ being a metal containing group in the case that $Y^1$ is a leaving group. The bridging group R and the X substituents are defined as herein before.

The invention also relates to a process for the preparation of a ligand precursor of formula (4) by a cross-coupling reaction of one 2-indenyl precursor of formula (5) with one cyclopentadienyl precursor of formula (6) with a bridging precursor R $(Y^2)_2$:

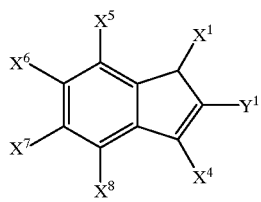

(5)

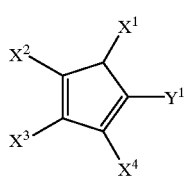

(6)

wherein:
  $X^1$ to $X^8$: are substituents,
  $Y^1$ and $Y^2$ are either a leaving group or a metal containing group,
  R is a bridging group, comprising the step of reacting 1 equivalent of the 2-indenyl precursor and 1 equivalent of the cyclopentadienyl precursor with 1 equivalent of the bridging precursor, $Y^2$ being a leaving group in the case that $Y^1$ is a metal containing group and $Y^2$ being a metal containing group in the case that $Y^1$ is a leaving group. The bridging group R and the X substituents are defined as herein before. A cross-coupling reaction is a reaction of an organometallic reagent with an organic compound substituted with a leaving group. In such reaction, the carbon-atom containing the organometallic group and the carbon atom containing the leaving group are coupled through C—C bond formation. Examples of leaving groups (denoted as Y above) are: halogens, diazonium groups, sulphonates, phosphates, phosphites, sulphides, sulphoxides, sulphones, selenides, carboxylates, ethers, silicon ethers, germanium ethers. An organometallic group is a group with formula —$M^m(Q^1)_n$.

Wherein:
  M: is an element of group 1–14 of the Periodic Table, except hydrogen and carbon
  m: is the valence of M.
  $Q^1$: is a substituent of M, for example halogen, hydroxy, alkyl, alkenyl, aryl, alkoxy, alkenoxy, aryloxy, trialkylsilyloxy, trialkenylsilyloxy, triarylsilyloxy, alkylsulphide, alkenylsulphides, arylsulphides, dialkylamides, dialkenylamides, diarylamides, alkylalkenylamides, alkylarylamides, alkenylarylamides. 2 or more substituents $Q^1$ can be connected to form a ring structure.
  n is the number of substituents $Q^1$ on M.

The organometallic group can be neutral when n=m−1, or anionic, when n=m. In a preferred embodiment one of the leaving groups $Y^1$ or $Y^2$ is boronic acid. In that case the ligand . . . the ligand precursors according to the invention (according to formula 3) is by reacting 1 equivalent of an indenyl-2-boronic acid and 1 equivalent of a boronic acid substituted cyclopentadienyl containing compound with 1 equivalent of $R(Y^2)_2$, or by reacting 1 equivalent of an indenyl-2-$Y^1$ and 1 equivalent of a cyclopentadienyl containing compound substituted with an $Y^1$-group with 1 equivalent of R-(boronic acid)$_2$, wherein $Y^1$ is a leaving group and R is a bridging group.

In this process the boronic acid substituted cyclopentadienyl containing compound preferably is an indenyl-2-boronic acid or the cyclopentadienyl containing compound substituted with an Y-group is an indenyl-2-Y. The leaving group in this case $Y^2$ can be halogen or a sulphonate. The leaving group preferably is bromine. Instead of a boronic acid also derivatives thereof, for example esters, can be used. The method described in the state of the art, for instance in WO-A-94/11406, for the preparation of the ligand precursors using a 2-indanone has the disadvantage that the yield of ligand precursor is low. Further disadvantages are that 2-indanones are expensive and that a lot of ligand precursors can not be prepared by using this method.

To prepare the ligand precursors according to formula (4) in the preferred embodiment, 2 equivalents of an indenyl-2-boronic acid are reacted with 1 equivalent of $R(Y^2)2$ or 2 equivalents of indenyl-2-$Y^1$ are reacted with 1 equivalent of R(boronic acid)$_2$.

The indenyl-2-boronic acid and the boronic acid substituted cyclopentadienyl containing compound are prepared by contacting of an indene substituted with a halogen on the 2-position or an cyclopentadiene containing compound, substituted with a halogen with magnesium to form a Grignard solution which reacts with a trialkoxyborane.

Examples of trialkoxyboranes are trimethoxyborane, triethoxyborane, tributoxyborane and triisopropoxyborane.

The indenyl compounds according to the invention can be prepared via different synthesis routes, consisting of synthesis steps known as such. They can for example be prepared by converting a ligand precursor into its dianion. Compounds that are suitable for converting the ligand precursor into the dianion are organometallic compounds, amines, metal hydrides and alkaline or alkaline earth metals. Organolithium, organomagnesium and organosodium compounds can for example be used for this purpose, but also sodium or potassium. In particular organolithium compounds are highly suitable, preferably methyl-lithium or n-butyl-lithium.

The dianion thus prepared is subsequently converted into the indenyl compound of the invention by trans-metalation with a compound of a transition metal from groups 3, 4, 5 or 6 of the Periodic System of Elements (M in formula (1)). See for example EP-A-420,436, EP-A-427,697. The process described in NL-A-91,011,502 is particularly suitable. Examples of transition metal compounds that are suitable for trans-metalation are TiCl$_4$, ZrCl$_4$, HfCl$_4$, Zr(OBu)$_4$ and Zr(OBu)$_2$Cl$_2$. The trans-metalation is preferably carried out as in NL-A-91,011,502, in a solvent or in a combination of solvents that weakly coordinate to transition metals from the groups 3, 4, 5 or 6 with at most 1 mole equivalent, relative to the transition metal compound started from, of a Lewis base of which the conjugated acid has a p$K_a$ greater than −2.5. Examples of suitable solvents/dispersants (pKa of conjugated acid≦−2.5) are ethoxyethane, dimethoxyethane, isopropoxyisopropane, n-propoxy-n-propane, methoxybenzene, methoxymethane, n-butoxy-n-butane, ethoxy-n-butane and dioxane. Part of the reaction medium may consist of hydrocarbons (hexane and the like).

The indenyl compounds according to the invention can be used, optionally in the presence of a cocatalyst, for the polymerisation of one or more olefins.

For example, the cocatalyst can be an organometallic compound. The metal of the organometallic compound can be selected from group 1, 2, 12 or 13 of the Periodic Table of Elements. Suitable metals include, for example and without limitation, sodium, lithium, zinc, magnesium, and aluminium, with aluminium being preferred. At least one hydrocarbon radical is bonded directly to the metal to provide a carbon-metal bond. The hydrocarbon group used in such compounds preferably contains 1–30, more preferably 1–10 carbon atoms. Examples of suitable compounds include, without limitation, amyl sodium, butyl lithium, diethyl zinc, butyl magnesium chloride, and dibutyl magnesium. Preference is given to organoaluminium compounds, including, for example and without limitation, the following: trialkyl aluminium compounds, such as triethyl aluminium and tri-isobutyl aluminium; alkyl aluminium hydrides, such as di-isobutyl aluminium hydride; alkylalkoxy organoaluminium compounds; and halogen-containing organoaluminium compounds, such as diethyl aluminium chloride, diisobutyl aluminium chloride, and ethyl aluminium sesquichloride. Preferably, aluminoxanes are selected as the organoaluminium compound.

The aluminoxanes can also be aluminoxanes containing a low amount of trialkylaluminium; preferably 0.5 to 15 mol % trialkylaluminium. In this case the amount of trialkylaluminium is more preferably 1–12 mol % trialkylaluminium.

In addition or as an alternative to the organometallic compounds as the cocatalyst, the catalyst composition of the present invention can include a compound which contains or yields in a reaction with the transition metal complex of the present invention a non-coordinating or poorly coordinating anion. Such compounds have been described for instance in EP-A-426,637, the complete disclosure of which is incorporated herein by reference. Such an anion is bonded sufficiently unstably such that it is replaced by an unsaturated monomer during the co-polymerisation. Such compounds are also mentioned in EP-A-277,003 and EP-A-277,004, the complete disclosures of which are incorporated herein by reference. Such a compound preferably contains a triaryl borane or a tetraaryl borate or an aluminium or silicon equivalent thereof. Examples of suitable cocatalyst compounds include, without limitation, the following:

dimethyl anilinium tetrakis (pentafluorophenyl) borate $[C_6H_5N(CH_3)_2H]^+$ $[B(C_6F_5)_4]^-$;

dimethyl anilinium bis (7,8-dicarbaundecaborate)-cobaltate (III);

tri(n-butyl)ammonium tetraphenyl borate;

triphenylcarbenium tetrakis (pentafluorophenyl) borate;

dimethylanilinium tetraphenyl borate;

tris(pentafluorophenyl) borane; and tetrakis(pentafluorophenyl) borate.

As described for instance in EP-A-500,944, the complete disclosure of which is incorporated herein by reference, the reaction product of a halogenated transition metal complex and an organometallic compound, such as for instance triethyl aluminium (TEA), can also be used.

The molar ratio of the cocatalyst relative to the transition metal complex, in case an organometallic compound is selected as the cocatalyst, usually is in a range of from about 1:1 to about 10,000:1, and preferably is in a range of from about 1:1 to about 2,500:1. If a compound containing or yielding a non-coordinating or poorly coordinating anion is selected as cocatalyst, the molar ratio usually is in a range of from about 1:100 to about 1,000:1, and preferably is in a range of from about 1:2 to about 250:1.

As a person skilled in the art would be aware, the transition metal complex as well as the cocatalyst can be present in the catalyst composition as a single component or as a mixture of several components. For instance, a mixture may be desired where there is a need to influence the molecular properties of the polymer, such as molecular weight and in particular molecular weight distribution.

The indenyl compound according to the invention can be used by a method known as such as a catalyst component for the polymerisation of an olefin.

The invention relates in particular to a process for the polymerisation of (an) α-olefin(s). The α-olefin(s) is/are preferably chosen from the group comprising ethylene, propylene, butene, pentene, hexene heptene and octene, while mixtures can also be used. More preferably, ethylene and/or propylene is/are used as α-olefin. The use of such olefins leads to the formation of crystalline polyethylene homopolymers and copolymers of both low and high density (HDPE, LDPE, LLDPE, etc.), and polypropylene homopolymers and copolymers (PP and EMPP). The monomers needed fur such products and the processes to be used are known to the skilled in the art.

The process according to the invention is also suitable for the preparation of amorphous or rubbery copolymers based on ethylene and another α-olefin. Propylene is preferably used as the other α-olefin, so that EPM rubber is formed. It is also possible to use a diene besides ethylene and the other α-olefin, so that a so-called EADM rubber is formed, in particular EPDM (ethylene propylene diene rubber).

The catalyst composition according to the invention can be used supported as well as non-supported. The supported catalysts are used mainly in gas phase and slurry processes. The carrier used may be any carrier known as carrier material for catalysts, for instance silica, alumina or $MgCl_2$.

Preferably, the carrier material is silica.

Polymerisation of the olefin can be effected in a known manner, in the gas phase as well as in a liquid reaction medium. In the latter case, both solution and suspension polymerisation are suitable, while the quantity of transition metal to be used generally is such that its concentration in the dispersion agent amounts to $10^{-8}$–$10^{-4}$ mol/l, preferably $10^{-7}$–$10^{-3}$ mol/l.

The process according to the invention will hereafter be elucidated with reference to a polyethylene preparation known per se, which is representative of the olefin polymerisations meant here. For the preparation of other polymers on the basis of an olefin the reader is expressly referred to the multitude of publications on this subject.

The preparation of polyethylene relates to a process for homopolymerisation or copolymerisation of ethylene with one or more α-olefins having 3–12 carbon atoms and optionally one or more non-conjugated dienes. The a-olefins that are suitable in particular are propylene, butene, hexene and octene. Suitable dienes are for instance 1,7-octadiene and 1,9-decadiene. It has been found that the catalyst composition of the present invention is especially suitable for solution or suspension polymerisation of ethylene.

Any liquid that is inert relative to the catalyst system can be used as dispersion agent in the polymerisation. One or more saturated, straight or branched aliphatic hydrocarbons, such as butanes, pentanes, hexanes, heptanes, pentamethyl heptane or mineral oil fractions such as light or regular petrol, naphtha, kerosine or gas oil are suitable for that purpose. Aromatic hydrocarbons, for instance benzene and toluene, can be used, but because of their cost as well as on account of safety considerations, it will be preferred not to use such solvents for production on a technical scale. In polymerisation processes on a technical scale, it is preferred therefore to use as solvent the low-priced aliphatic hydrocarbons or mixtures thereof, as marketed by the petrochemical industry. If an aliphatic hydrocarbon is used as solvent, the solvent may yet contain minor quantities of aromatic hydrocarbon, for instance toluene. Thus, if for instance methyl aluminoxane (MAO) is used as cocatalyst, toluene can be used as solvent in order to supply the MAO in dissolved form to the polymerisation reactor. Drying or purification is desirable if such solvents are used; this can be done without problems by the average person skilled in the art.

Such a solution polymerisation is preferably carried out at temperatures between 150° C. and 250° C.; in general, a suspension polymerisation takes place at lower temperatures, preferably below 100° C.

The polymer solution resulting from the polymerisation can be worked up by a method known per se. In general the catalyst is de-activated at some point during the processing of the polymer. The de-activation is also effected in a manner known per se, e.g. by means of water or an alcohol. Removal of the catalyst residues can mostly be omitted because the quantity of catalyst in the polymer, in particular the content of halogen and transition metal is very low now owing to the use of the catalyst system according to the invention.

Polymerisation can be effected at atmospheric pressure, but also at an elevated pressure of up to 500 MPa, continuously or discontinuously. If the polymerisation is carried out under pressure the yield of polymer can be increased additionally, resulting in an even lower catalyst residue content. Preferably, the polymerisation is performed at pressures between 0.1 and 25 MPa. Higher pressures, of 100 MPa and upwards, can be applied if the polymerisation is carried out in so-called high-pressure reactors. In such a high-pressure process the catalyst according to the present invention can also be used with good results.

The polymerisation can also be performed in several steps, in series as well as in parallel. If required, the catalyst composition, temperature, hydrogen concentration, pressure, residence time, etc. may be varied from step to step. In this way it is also possible to obtain products with a wide molecular weight distribution.

The invention will now be elucidated by means of the following non-restrictive examples.

EXAMPLES

Example I

The Synthesis of [ortho-bis (4-phenyl-2-indenyl)-benzene]zirconiumdichloride

I.1 4-phenyl-2-bromo-indan-1-one

4-Phenylindan-1-one was synthesised according to methods known in literature. 4-Phenylindan-1-one (20.83 g, 0.10 mol) was dissolved in dry dichloromethane (250 ml). While cooled with an ice-bath, a solution of bromine (16.30 g, 0.102 mol) in dry dichloromethane (200 ml) was added via a dropping funnel with a teflon tap during 1 hour. The yellow solution was then allowed to warm to room temperature and stirred at room temperature for 1 hour. The mixture was poured in water, and the organic phase was extracted with saturated sodium hydrogen carbonate and with, saturated brine. The organic phase was dried over sodium sulphate and filtered. The solvent was removed in vacuo to leave a yellow oil (31.02 g, quantitative) NMR indicates purity>90%. The product was used as such in the next step.

I.2 4-phenyl-2-bromo-indan-1-ol

The crude 4-phenyl-2-bromo-indan-1-one (31.02 g, ~0.10 mol) was dissolved in a mixture of tetrahydrofurane (THF) (100 ml) and methanol (50 ml). While cooled with an ice-bath, sodium borohydride (6.67 g, 0.17 mol) was added in portions. Gas evolved vigorously, and the temperature rose to reflux. After stirring overnight at ambient temperature, the mixture was quenched with ice and acidified with hydrochloric acid. Ether and water were added, and after shaking the organic phase was separated. The aqueous phase was extracted with ether twice, and the combined organic phases were extracted with saturated brine. The organic phase was dried over sodium sulphate and filtered. The solvent was removed in vacuo to leave a yellow oil (36.9 g, quantitative). The oil was dissolved in warm toluene (100 ml) and filtered warm. To the clear filtrate was added warm hexane (800 ml), resulting in crystallisation of fluffy microneedles. These were filtered, washed with hexane, and dried. Yield 25.08 g (87%).

I.3 4-phenyl-2-bromoindene

A solution of 4-phenyl-2-bromo-indan-1-ol (13.51 g, 46.7 mmol) in toluene (200 ml) was boiled in a Dean-Stark apparatus with p-toluene sulphonic acid (4 g) for 30 min, after which period the expected amount of water was collected. The reaction mixture was cooled and poured onto water. Ether and a dilute sodium hydrogen carbonate solution in water were added, and the aqueous phase was separated. The organic phase was extracted with dilute sodium hydrogen carbonate three times. The organic phase was then dried over sodium sulphate and filtered. The solvent was removed in vacuo to leave a yellow oil. Kugelrohr distillation (0.02 bar, 170–180° C.) afforded 7.52 g of product (59%).

I.4 (4-phenylinden-2-yl)-boronic acid

Under an atmosphere of dry nitrogen, magnesium turnings (0.86 g, 35 mmol) covered with dry THF (5 ml) were activated by 1,2-dibromoethane. Consecutively, a solution of 4-phenyl-2-bromoindene (4.80 g, 17.7 mmol) in dry THF (20 ml) was added slowly. The brown solution was stirred at room temperature for 1 hour.

Then, the Grignard solution was added to a solution of tri-isopropoxy-borane (4.6 ml, 20 mmol) in dry THF (10 ml) at −80° C. via a syringe. The solution was allowed to rise to room temperature, resulting in precipitation. At room temperature, it turned to a solution again, brown coloured. After stirring overnight at ambient temperature, the mixture was quenched with ice and acidified with hydrochloric acid. Ether was added, and after shaking, the organic phase was separated. The aqueous phase was extracted with ether once more, and the combined organic phases were extracted with saturated brine. The organic phase was dried over sodium sulphate and filtered. The solvent was removed in vacuo to leave a yellow oil (4.39 g). The oil was dissolved in a small amount of ether, and the product obtained by precipitation into hexanes (1.40 g, 34%).

I.5 ortho-bis(2-(4-phenylindenyl))-benzene

A 25 cc three-necked flask fitted with a reflux condenser and nitrogen inlet, was charged with (4-phenylinden-2-yl)-boronic acid (1.32 g, 5.6 mmol) and ortho-dibromobenzene (0.64 g, 2.7 mmol). The flask was brought under an atmosphere of dry nitrogen by purging for approx. 1 hour. Then, dimethoxyethane (16 ml) and water (8 ml) were added, followed by potassium carbonate (0.85 g). The two phase system of two solutions was deoxygenated by consecutively evacuation until reflux and letting nitrogen gas in three times. Palladium-tetrakis(triphenylphosphine) (0.15 g, 0.13 mmol, 2.3 mol %) was added, and the yellow mixture was heated to reflux. During this process, the colour gradually changed within one hour to brown-yellow. Reflux was continued for a period of 2 hours. After cooling, the mixture was poured into a dilute hydrochloric acid solution (50 ml) and ether (50 ml). After shaking well, the layers were separated. The organic phase was separated, and extracted consecutively with dilute hydrochloric acid twice and with water once. The organic phase was dried over sodium sulphate, filtered, and evaporated to dryness. The oily residue was subdued to column chromatography on silica, using hexane with increasing amounts of ethyl acetate as eluent. The combined product fractions were treated with active carbon while boiling in hexane. After filtration and evaporation to dryness, 0.59 g of pure product remained (1.2 mmol, 47 %).

I.6 [ortho-bis(4-phenyl-2-indenyl)-benzene]zirconiumdichloride

To a solution of ortho-bis(4-phenyl-2-indenyl)-benzene (0.56 g, 1.22 mmol) in dry ether (8 ml) was added n-butyllithium (1.6 M in hexanes, 1.5 ml, 2.4 mmol) at 0° C. by ice-bath cooling. The resultant suspension was stirred at room temperature for 5 hour. Meanwhile, a suspension of zirconium tetrachloride (0.2843 g, 1.22 mmol) in dry ether (7 ml) was prepared. The suspensions (of dianion in ether and of zirconium tetrachloride in ether) were cooled in an acetone/dry ice bath, and mixed via a bended connection tube. The temperature was allowed to rise to room temperature. After stirring overnight, part of the ether was evaporated under vacuo and the cold suspension was filtered. The residue was washed with dry ether/hexane 1:1 v/v mixture (5 ml) two times. The residue was dissolved partly in hot toluene (20 ml), and the suspension filtered hot under an atmosphere of dry nitrogen. The filtrate was partly evaporated to ~10 ml. Standing for three days gave fine yellow crystals of one isomer (fraction A, 0.11 g, 15%, purely consisting of isomer 1). The filtrate was partly evaporated, diluted with dry hexanes to result in complete precipitation. Hexanes were evaporated, and solution in toulene made again. The hazy solution was filtered, and volume reduced to ~3 ml. Upon standing a second fraction consisting of fine yellow dots contained 25–30% of an other isomer (fraction B, 0.10 g, 13%, consisting of 70–75% of isomer 1, and 25–30% of isomer 2). The filtrate was diluted with dry hexanes, and repeated cycles of boiling and cooling resulted in the formation of yellow grains (fraction C, 0.18 g, 24%, consisting of ~40% of isomer 1, and 60% of isomer 2).

Example II

The Synthesis of [ortho-bis(5-phenyl-2-indenyl)-benzene]zirconiumdichloride

II.1. 2-(4-bromobenzyl)malonate

A one-necked flask of 2 l was charged with 17.5 g (760 mmol) of sodium and 500 ml of ethanol. The mixture was stirred overnight. Via a droppingfunnel a solution of 128.1 g (800 mmol) of diethylmalonate in 400 ml of ethanol was added. A solution of 98.4 g of p-bromobenzylbromide in 100 ml of ethanol was added to the anion of diethylmalonate in approximately 40 minutes and after completion the mixture was heated for 4 hours to reflux. After evaporation of the solvent the product was used in the next step without further purification.

II.2. 2-(4-bromobenzyl)malonic acid

The product obtained in the synthesis of 2-(4-bromobenzyl)malonate was directly used for the synthesis of 2-(4-bromobenzyl)malonic acid. To a one-necked flask, fitted with a reflux condenser, the crude malonate was added to a solution of 106 g of potassiumhydroxide in 110 ml of water. The reaction mixture was stirred for 18 hours at reflux. To the reaction mixture was added 3.5 l of water and approximately 240 ml hydrochloric acid. The water layer was extracted with diethylether. The diethylether was evaporated after which a partly hydrolysed product was obtained. The product was hydrolysed again with 110 g potassiumhydroxyde and 200 ml water at reflux for 18 hours. After work-up as described previously 88.0 g of 2(4-bromobenzyl)malonic acid was obtained. Yield 84%.

II.3. 3-(4-bromobenzyl)propionic acid

A one-necked flask of 250 ml was charged with 82.8 g (300 mmol) of 2(4-bromobenzyl)malonic acid This was heated to 165° C. for 2 hours. 62.0 g of 3-(4-bromobenzyl)propionic acid (89%) was obtained.

II.4. 3-(4-bromobenzyl)propionic acid chloride.

To a three-necked flask of 250 ml, fitted with a reflux condenser, 62.0 g (270 mmol) 3-(4-bromobenzyl)propionic acid was added. A droppingfunnel was charged with 80 ml of thionylchloride. This was added dropwise to the solid propionic acid. After the addition was complete the reaction mixture was heated to reflux for 1 hour. The thionylchloride was removed under reduced pressure. Toluene was added and evaporated from the mixture to remove the last parts of the thionylchloride. The solid product was used directly in the next synthesis II.5. 6-bromoindan-1-one A three-necked flask of 1 l, equipped with a reflux condenser, was charged with 50 g aluminiumtrichloride dissolved in 500 ml $CS_2$. To the mixture a solution of the crude acidchloride in 100 ml of $CS_2$ was added. After the addition the mixture was allowed to reflux for 3 hours. The content of the flask was poured on ice and hydrochloric acid was added until pH=1. The water layer was extracted with diethylether. The diethylether was washed once with water and once with a saturated sodiumchloride solution. The ether layer was dried over sodiumsulphate. The sodiumsulphate was filtered off and the ether was evaporated. The product was recrystallized from toluene and petroleum ether. 26.6 g of 6-bromoindan-1-one was obtained (47%).

II.6. 6-phenylindan-1-one

To a three-necked flask of 500 ml, fitted with a condenser, was added 150 ml N-methylpyrrolidon (NMP), 10.45 g (49.5 mmol) 6-bromoindan-1-one and 19.9 g (54.2 mmol) of tributylphenyltin. To this mixture was added 1.05 g (1.50 mmol) of bis(triphenyl-phosphine)palladium(II)chloride. The reaction mixture was heated to 85° C. for 4 h, followed by stirring for 4 hours at ambient temperature. A solution of 23 g of potassiumfluoride in 50 ml of water was added. The solids were filtered off and the filtrate was diluted with diethylether, washed once with water and once with saturated sodiumchloride solution. The ether layer was evaporated under reduced pressure and the solid material was crystallised from toluene, petroleum ether. A total of 5.29 g of 6-phenylindan-1-one was obtained, yield 51.4%.

II.7. 6-phenyl-2-bromoindanone

To a three-necked flask of 250 ml was added 10.35 g (49.7 mmol) of 6-phenylindan-1-one and 70 ml of dry dichloromethane. Bromine, 8.4 g (53 mmol), dissolved in 80 ml of dichloromethane was added via a droppingfunnel over a period of 30 minutes. After the addition was complete the mixture was stirred for 15 hours. To the reaction mixture water was added. The water layer and dichloromethane layer were separated. The organic layer was washed once with water. The water layer was extracted once with diethylether. The combined organic layers were washed once with saturated sodumbicarbonate solution. The solvent from the organic layers was evaporated under reduced pressure. The remaining solid material was the bromonated compound. Yield 12.84 g (90%).

II.8. 6-phenyl-2-bromoindanol

To a three-necked flask of 250 ml, fitted with a condenser, was added 3.55 g (12.4 mmol) of 6-phenyl-2-bromo-1-indanone, 100 ml of tetrahydrofuran (THF) and 100 ml of absolute ethanol. A dark red solution was formed and 0.40 g (10 mmol) of sodiumboronhydride was added in small portions. The mixture was stirred for 15 hours at room temperature. The mixture was poured onto ice and a 5% hydrochloric acid solution was added. The water layer was extracted 3 times with ether and the combined ether layer washed 2 times with a saturated NaCl solution. The ether was evaporated under reduced pressure yielding 2.57 g (8.89 mmol) of 6-phenyl-2-bromoindanol (72%).

II.9. 5-phenyl-2-bromoindene

To a one-necked flask of 500 ml, fitted with an dropping funnel and on top of the funnel a condenser, was added 10.19 g (35.2 mmol) of 6-phenyl-2-bromoindanol, 0.671 g (0.10 mol %) p-toluenesulfonic acid and 350 ml of toluene. After 7 hours of refluxing the mixture was diluted with ether and extracted with water and water/NaHCO$_3$. The organic layer was dried over Na$_2$SO$_4$. The Na$_2$SO$_4$ was filtered off and the filtrate was evaporated under reduced pressure. The solid material was dissolved in hot n-pentane and recrystallized giving 7.56 g (27.9 mmol) of 5-phenyl-2-bromoindene. Yield 79%.

II.10 (5-phenylinden-2-yl)-boronic acid

Under an atmosphere of dry nitrogen, magnesium turnings (0.61 g, 25 mmol) covered with dry THF (5 ml) were activated by 1,2-dibromoethane. Consecutively, a solution of 5-phenyl-2-bromoindene (3.40 g, 12.5 mmol) in dry THF (20 ml) was added slowly. The brown solution was stirred at room temperature for 3 hours. Then, the Grignard solution was added to a solution of tri-isopropoxy-borane (6 ml, 25 mmol) in dry THF (20 ml) at −80° C. via a syringe. The solution was allowed to rise to room temperature. After stirring overnight at ambient temperature, the mixture was quenched with ice and acidified with hydrochloric acid. Ether was added, and after shaking, the organic phase was separated. The aqueous phase was extracted with ether once more, and the combined organic phases were extracted with saturated brine. The organic phase was dried over sodium sulphate and filtered. The solvent was removed in vacuo to leave a yellow oil (2.93 g). The oil was dissolved in a small amount of ether, and the product obtained by precipitation into hexanes. Yield 1.23 g (42%).

II.11 ortho-bis (5-phenyl-2-indenyl))-benzene

A 25 cc three-necked flask fitted with a reflux condenser and nitrogen inlet, was charged with (4-phenylinden-2-yl)-boronic acid (1.12 g, 4.74 mmol) and ortho-dibromobenzene (0.53 g, 2.26 mmol). The flask was brought under an atmosphere of dry nitrogen by purging for approx. 1 hour. Then, dimethoxyethane (16 ml) and water (8 ml) were added, followed by potassium carbonate (0.76 g). The two phase system of two solutions was deoxygenated by consecutively evacuation until reflux and letting nitrogen gas in three times. Palladium-tetrakis(triphenylphosphine) (0.06 g, 0.05 mmol, 2 mol %) was added, and the yellow mixture was heated to reflux. The colour gradually changed within one hour to brown-yellow. Reflux was continued overnight. After cooling, the mixture was poured into a dilute hydrochloric acid solution (50 ml) and ether (50 ml). After shaking well, the layers were separated. The organic phase was separated, and extracted consecutively twice with dilute hydrochloric acid and twice with water. The organic phase was dried over sodium sulphate, filtered, and evaporated to dryness (1.31 g). The oily residue was subdued to column chromatography on silica, using hexane with increasing amounts of ethyl acetate as eluent. The fractions containing the product were collected. The combined product fractions amounted 0.87 g of pure product (1.9 mmol, 84%)

II.12 [ortho-bis(5-phenyl-2-indenyl)-benzene] zirconiumdichloride

To a solution of ortho-bis(5-phenyl-2-indenyl)-benzene (0.85 g, 1.85 mmol) in dry ether (10 ml) was added n-butyllithium (1.6 M in hexanes, 2.3 ml, 3.7 mmol) at 0° C. by ice-bath cooling. The resultant dark-red solution was stirred at room temperature for 5 hour.

Meanwhile, a suspension of zirconium tetrachloride (0.431 g, 1.85 mmol) in dry ether (10 ml) was prepared.

The solution of dianion in ether and the suspension of zirconium tetrachloride in ether were cooled in an acetone/dry ice bath, and mixed via a bended connection tube. The temperature was allowed to rise to room temperature, resulting in a orange-red suspension. After stirring overnight, a lemon-yellow suspension was obtained. The suspension was filtered and the solids were washed with dry ether/hexane 1:1 v/v mixture (5 ml) two times. The remaining solid was dissolved partly in hot toluene (20 ml), and the suspension filtered hot under an atmosphere of dry nitrogen. After standing overnight, the hazy filtrate was boiled with norit, and filtered hot. The clear yellow solution was evaporated partly, and prolonged standing in the refrigerator gave 0.14 g of yellow powder (12%), containing a 1:1 mixture of both 2 isomers as indicated by NMR.

Example III

The Synthesis of [ortho-bis(2-indenyl)benzene] zirconiumdichloride and [ortho-bis(2-indenyl) benzene]hafniumdichloride III.1 2-bromoindene To 1009 g of 2-bromo-1-indanol (4.74 mol) was added 800 ml of toluene and 25 g of Amberlist® 15 (acid ion exchanging resin). The mixture was warmed to reflux for 2 hours followed by 4 hours of azeotropical removal of water. The Amberlist was filtered off and the toluene was evaporated from the filtrate. The residue was distilled under reduced pressure yielding 400 g (43%) of a light yellow oil which solidified upon standing.

III.2 (2-indenyl) boronic acid

Magnesium turnings (9.72 mol, 0.40 mol) covered with dry THF (50 ml) were activated with 1,2-dibromoethane. Then, a solution of 2-bromoindene (39.01 g, 0.20 mol) in dry THF (200 ml) was added slowly during 45 min under cooling with an ice-bath to maintain the temperature below 20° C. The mixture was stirred at room temperature for 2 h after complete addition.

Via a syringe, the Grignard solution was decanted from the excess magnesium turnings and added slowly to a solution of tri(isopropoxy)borane (92 ml, 0.40 mol) in dry THF (250 ml) at −30 to −50° C. The temperature was allowed to rise to room temperature, and stirring was continued overnight. The mixture was quenched with water, then dilute hydrochloric acid (25 ml concentrated (37%) in 250 ml water) was added. The mixture was stirred for 30 min, then transferred into a separatory funnel. The organic phase was separated, and the aqueous phase extracted with ether three times. The combined organic phases were extracted three times with a small amount of saturated brine. The organic phase was dried over sodium sulphate, filtered, and evaporated to dryness. The residue was dissolved in boiling ether (200 ml), then hexanes were added (400 ml). Quick filtration of the hazy solution removed some impurities. The clear filtrate was evaporated slowly and partly on the rotary evaporator to afford white powder. After filtering, washing and drying, the total yield of product amounted 18.54 g, 58%).

III.3 ortho-bis(2-indenyl)benzene

A 1000 ml three-necked flask fitted with a reflux condenser and nitrogen inlet, was charged with indenyl-2-boronic acid (14.80 g, 93 mmol) and ortho-dibromobenzene (10.39 g, 44.05 mmol). The flask was brought under an atmosphere of dry nitrogen by purging for approx. 1 hour. Then, dimethoxyethane (100 ml) and water (50 ml) were added, followed by potassium carbonate (13.92 g, 101 mmol). The two phase system of two solutions was deoxygenated by consecutively evacuation until reflux and letting nitrogen gas in three times. Palladium-tetrakis (triphenylphosphine) (0.62 g, 0.54 mmol, 1.2%) was added, and the yellow mixture was heated to reflux. The colour gradually changed within one hour to brown-yellow. Reflux was continued for a period of 16 hour. After cooling, the mixture was poured into a dilute hydrochloric acid solution (500 ml) and ether (500 ml). After shaking well, the layers were separated. The organic phase was separated, and extracted consecutively with dilute hydrochloric acid twice and with water twice. The organic phase was dried over sodium sulphate, filtered, and evaporated to dryness. The residue was dissolved in a boiling mixture of ethyl acetate (100 ml) and hexanes (500 ml). The brown solution was treated with active carbon, and filtered to give an orange solution. After evaporation to dryness, the orange solid was crystallised from ethanol (96%, 1 L) treated with active carbon again giving a yield of 11.56 g (85.6%) of product.

III.4 ortho-bromo-(2-indenyl)benzene

A 2000 ml three-necked flask fitted with a reflux condenser and nitrogen inlet, was charged with indenyl-2-boronic acid (32.0 g, 0.20 mol) and ortho-dibromobenzene (96.0 g, 0.41 mol). The flask was brought under an atmosphere of dry nitrogen by purging for approx. 1 hour. Then, dimethoxyethane (600 ml) and water (300 ml) were added, followed by potassium carbonate (31.60 g, mmol). The two phase system of two solutions was deoxygenated by consecutively evacuation until reflux and letting nitrogen gas in three times. Palladium-tetrakis(triphenylphosphine) (1.20 g, 2 mmol, 0.5 mol %) was added, and the yellow mixture was heated to reflux. The colour gradually changed within one hour to brown-yellow. Reflux was continued for a period of 16 hour. After cooling, the mixture was poured into a dilute hydrochloric acid solution (1000 ml) and ether (500 ml). After shaking well, the layers were separated. The organic phase was separated, and extracted consecutively with dilute hydrochloric acid twice and with water twice. The organic phase was dried over sodium sulphate, filtered, and evaporated to dryness. The residue was dissolved in boiling ethanol (500 ml) diluted with some acetone. Cooling gave 3.90 g of a white powder being the ortho-bis(2-indenyl) benzene (12.7 mmol, 12.7%). The filtrate was evaporated to dryness, and subdued to distillation in vacuo (0.46 mbar), distilling 28.85 g (0.106 mol, 53%) of pure product.

III.5 [ortho-bis (2-indenyl)benzene]zirconiumdichloride

A 1000 ml three-necked flask was charged with ortho-bis (2-indenyl)benzene (7.70 g, 25 mmol) and brought under an atmosphere of dry nitrogen by evacuation/letting nitrogen in. Dry and oxygen free ether (100 ml) was added. The resultant suspension was cooled to 0° C. by ice-bath, and a solution of n-butyllithium (1.6 M in hexanes, 31.1 ml, 50 mmol) was added. The resultant suspension was stirred at room temperature for 4 hour.

Meanwhile, a suspension of zirconium tetrachloride (5.83 g, 25 mmol) in dry ether (50 ml) was prepared: cooled ether (−20° C.) was added to the zirconium tetrachloride contained in 100 ml Schlenk flask under nitrogen atmosphere via a bended connection tube. Then, the temperature was allowed to rise to room temperature, and stirring was continued for 30 min. The suspensions (of dianion in ether and of zirconium tetrachloride in ether) were cooled in an acetone/dry ice bath, and mixed via a bended connection tube. The temperature was allowed to rise to room temperature. After stirring overnight, the suspension was filtered (under nitrogen atmosphere), and the solids washed with dry ether twice. The solid was dissolved partly in hot toluene, and the suspension filtered hot under an atmosphere of dry nitrogen. The clear yellow filtrates were cooled slowly to ambient temperature, giving yellow crystals of pure product (6.35 g, 13.7 mmol, 54.4%).

III.6 [ortho-bis(2-indenyl)benzene]hafniumdichloride

To a suspension of ortho-bis(2-indenyl)benzene (0.77 9, 2.5 mmol) in dry ether (10 ml) was added n-butyllithium (1.6 M in hexanes, 3.1 ml, 5 mmol) at 0° C. by ice-bath cooling. Initially, all dissolved, then a powder precipitated. The resultant suspension was stirred at room temperature for 4 hour. Meanwhile, a suspension of hafnium tetrachloride (0.800 g, 2.5 mmol) in dry ether (10 ml) was prepared: cooled ether (−20° C.) was added to the hafnium tetrachloride contained in 100 ml Schlenk flask under nitrogen atmosphere via a bended connection tube. Then, the temperature was allowed to rise to room temperature, and stirring was continued for 30 min.

The suspensions (of dianion in ether and of hafnium tetrachloride in ether) were cooled in an acetone/dry ice bath, and mixed via a bended connection tube. The temperature was allowed to rise to room temperature. After stirring overnight, the suspension was filtered (under nitrogen atmosphere), and the solids washed with dry ether (5 ml) three times. The solid was dissolved partly in hot toluene (100 ml), and the suspension filtered hot under an atmosphere of dry nitrogen. The clear yellow filtrate was cooled slowly to ambient temperature, giving yellow crystals of pure product (0.79 g, 57%). Another 12% yield was obtained by cooling of the filtrate to −20° C.

Example IV

The Synthesis of [ortho-bis(1-methyl-2-indenyl)-benzene]zirconiumdichloride

IV.1 ortho-bis(1-methyl-2-indenyl))-benzene 1.75 g. of the product from reaction III.3 was suspended in 40 ml ether (5.72 mmol). At −70°0 C., 2 equivalents of butyllithium was added (7.1 ml). the white suspension was stirred at room temperature for 4 hours. Then the suspension was cooled again and methyliodide was added (1.62 g). The mixture was stirred for 8 hours. The solvent was evaporated. The product was dissolved in ethanol and gave yellow crystals (0.83 g, 43%) at −20° C.

IV.2 [ortho-bis (1-methyl-2-indenyl)-benzene] zirconiumdichloride 0.85 g. (2.54 mmol) of the product from IV.1 was dissolved in 30 ml ether. at −70° C. 3.1 ml butyllithium was added. The reaction mixture was stirred at room temperature for 3 hours. At −70° C. 0.60 g. (2.54 mmol) zirconium tetrachloride was added. The suspension was stirred 8 hours whereafter the solvent was evaporated. The product was washed with 40 ml toluene and filtered off. The yellow residue was dried under evaporation.

Example V

The Synthesis of [2,2'-(1,2-phenyldiyl)-1,1'-dimethylsilyl-bis(indene)]zirconiumdichloride V.1. 1,2-phenylene-bis(2-indenyl)1,1'-dimethylsilyl To a solution of ortho-bis(2-indenyl)benzene (0.92 g, 3.0 mmol) in dry diethyl ether (15 ml) was added n-butyllithium in hexanes (3.8 ml, 1.6 M in hexanes, 6.0 mmol) under cooling with ice-bath. The temperature was allowed to rise to room temperature, and stirring was continued for 2 hour. More ether (25 ml) was added, and the suspension was cooled to −78° C. A solution of freshly distilled dimethyldichlorosilane (0.39 g, 3.0 mmol) in dry ether (5 ml) was added slowly via a syringe. The temperature was allowed to rise to room temperature, and the mixture stirred for 3 days. To the mixture was added water (60 ml), then 30 ml ethanol. The sticky powder was filtered off, and washed with ethanol to give a nice fluffy powder of pure product (0.67 g, 1.8 mmol, 62%).

V.2. [2,2'-(1,2-phenyldiyl)-1,1'-dimethylsilyl-bis(indene)] zirconiumdichloride

To a suspension of 1,2-phenylene-bis(2-indenyl)1,1'-dimethylsilyl (0.65 g, 1.80 mmol) in dry ether (11 ml) was added n-butyllithium (1.6 M in hexanes, 2.3 ml, 3.6 mmol) at 0° C. by ice-bath cooling. The suspension was stirred at room temperature for 5 hour.

Meanwhile, a suspension of zirconium tetrachloride (0.419 g, 1.8 mmol) in dry ether (7 ml) was prepared.

The suspensions (of dianion in ether and of zirconium tetrachloride in ether) were cooled in an acetone/dry ice bath, and mixed via a bended connection tube. The temperature was allowed to rise to room temperature. After stirring overnight, part of the ether was evaporated and the cold suspension was filtered. The residue was washed with dry ether (5 ml) three times. The residue was dissolved partly in hot toluene (20 ml), and the suspension filtered hot under an atmosphere of dry nitrogen. The slightly hazy yellow filtrate was filtered again, then the filtrate was partly evaporated, and the solution diluted with dry hexane to result in the precipitation of pure product (0.50 g, 0.96 mmol, 53%).

Example VI

The Synthesis of [2,2'-(1,2-phenyldiyl)-1,1'-diphenylsilyl-bis(indene)]zirconiumdichloride VI.1. 2,2'-(1,2-phenyldiyl)-1,1'-diphenylsilyl-bis(indene)

To a solution of ortho-bis(2-indenyl)benzene (0.92 g, 3.0 mmol) in dry ether (15 ml) was added n-butyllithium in hexanes (3.8 ml, 1.6 M in hexanes, 6.0 mmol) under cooling with ice-bath. The temperature was allowed to rise to room temperature, and stirring was continued for 2 hour. More ether (20 ml) was added, and the suspension was cooled to −78° C. A solution of diphenyl-dichlorosilane (0.76 g, 3.0 mmol) in dry ether (5 ml) was added slowly via a syringe. The temperature was allowed to rise to room temperature, and the mixture stirred for 6 days. To the mixture was quickly added water (30 ml), then ethanol (50 ml). The powder was filtered off, and washed with ethanol to give a fluffy powder of pure product (0.50 g, 1.1 mmol, 36%).

VI.2. [2,2'-(1,2-phenyldiyl)-1,1'-diphenylsilyl-bis(indene)] zirconiumdichloride To a suspension of 1,2-phenyldiyl-1,1'-dimethylsilyl-2,2'-indene (0.39 g, 0.80 mmol) in dry ether (5 ml) was added n-butyllithium (1.6 M in hexanes, 1.0 ml, 1.6 mmol) at 0° C. by ice-bath cooling. The resultant solution was stirred at room temperature for 5 hour.

Meanwhile, a suspension of zirconium tetrachloride (0.1866 g, 0.8 mmol) in dry ether (5 ml) was prepared.

The solution of dianion in ether and the suspension of zirconium tetrachloride in ether were cooled in an acetone/dry ice bath, and mixed via a bended connection tube. The temperature was allowed to rise to room temperature. After stirring overnight, part of the ether was evaporated in vacuo and the cold suspension was filtered. The residue was washed with dry ether (5 ml) three times. The residue was dissolved partly in hot toluene (10 ml), and the suspension filtered hot under an atmosphere of dry nitrogen. The slightly hazy yellow filtrate was filtered again, then the filtrate was partly evaporated. Yellow fine crystals separated (0.03 g, 6%).

Example VII

The Synthesis of [2,2'-(1,2-phenyldiyl)-1,1'-(1,2-ethanediyl)-bis(indene)]zirconiumdichloride VII.1. 2,2'-(1,2-phenyldiyl)-1,1'-(1,2-ethanediyl)-bis (indene)

To a solution of ortho-bis(2-indenyl)benzene (0.92 g, 3.0 mmol) in dry ether (15 ml) was added n-butyllithium in hexanes (3.8 ml, 1.6 M in hexanes, 6.0 mmol) under cooling with ice-bath. The temperature was allowed to rise to room temperature, and stirring was continued for 2 hour. More ether (20 ml) was added, and the suspension was cooled to −78° C. A solution of 1,2-dibromoethane (0.56 g, 3.0 mmol) in dry ether (5 ml) was added slowly via a syringe. The temperature was allowed to rise to room temperature, and the mixture stirred for 6 days. To the mixture was quickly added water (30 ml), then ethanol (50 ml). The powder was filtered off, and washed with ethanol to give a fluffy powder of almost pure product (fraction A, 0.22 g). The filtrate was evaporated to dryness, dissolved in hot acetone and filtered hot. The clear filtrate was diluted with water, and partly evaporated, resulting in the precipitation of a fine powder (fraction B, 0.71 g).

To obtain pure product, fraction A was crystallised from ethanol/acetone to give pure product (0.07 g, 7%). The evaporated mother liquor hereof, combined with fraction B, was dissolved in boiling hexane/ethyl acetate 4:1 v/v, treated with active carbon, and filtered hot to remove most of the starting material. Crystallisation from ethanol/acetone afforded another crop of product (0.20 g, 20%).

VII.2. [2,2'-(1,2-phenyldiyl)-1,1'-(1,2-ethanediyl)-bis (indene)]zirconiumdichloride To a suspension of 2,2'-(1,2-phenyldiyl)-1,1'-(1,2-ethanediylbis(indene) (0.27 g, 0.81 mmol) in dry ether (5 ml) was added n-butyllithium (1.6 M in hexanes, 1.0 ml, 1.6 mmol) at 0° C. by ice-bath cooling. The resultant suspension was stirred at room temperature for 5 hour. Meanwhile, a suspension of zirconium tetrachloride (0.1887 g, 0.81 mmol) in dry ether (5 ml) was prepared. The solution of dianion in ether and the suspension of zirconium tetrachloride in ether were cooled in an acetone/dry ice bath, and mixed via a bended connection tube. The temperature was allowed to rise to room temperature. After stirring overnight, part of the ether was evaporated under vacuo and the cold suspension was filtered. The residue was washed with dry ether (5 ml) three times. The residue was dissolved partly in hot toluene (40 ml), and the suspension filtered hot under an atmosphere of dry nitrogen. The clear filtrate separated crystals upon standing (0.147 g, 37%).

Example VIII

The Synthesis of [2,2'-bis(2-indenyl)biphenyl] zirconiumdichloride and [2,2'-bis(2-indenyl) biphenyl]hafniumdichloride VIII.1. 2,2'-dilithio-biphenyl bis trimethyl ethylene tiamine (TMEDA) adduct A 2000 ml three-necked flask, fitted with a reflux condenser and nitrogen inlet, was charged with butyllithium in hexanes (1 L, 1.6 mol). While cooling with an ice-bath, TMEDA (241 ml, 0.67 mol) was added slowly. During this process, a thick suspension formed that dissolved again at the end when all was added. Then, biphenyl (103 g, 0.67 mol) was added in portions. The mixture was slowly heated to 55° C., and that temperature was maintained for 2.5 hour. Cooling of the hazy and red-brown solution overnight at −20° C. gave yellow crystals in a hazy and red-brown solution. The mother liquor was decanted via a bended connection tube, and the residue washed with cold hexane twice. After drying, 131.57 g (0.33 mol, 49%) is obtained.

VIII.2. 2,2'- biphenyl boronic acid

A suspension of 2,2'-dilithio-biphenyl-bis TMEDA adduct (131.57 g, 0.33 mol) in dry ether (1000 ml) was cooled to −78° C. by a dry ice/acetone bath. Trimethoxyborane (225 ml, 1.98 mol) was added slowly via a syringe during 30 min. Initially, all yellow suspension quickly dissolved giving an orange-brown solution within the first 50 ml added; then, the reaction mixture turned into a white suspension, and finally, a clear solution was obtained. The reaction mixture was allowed to warm to room temperature, and stirred overnight. The mixture was quenched with water (300 ml), and stirred for 4 hour. Then, a dilute solution of hydrochloric acid (100 ml of 37% solution in 400 ml of water) was added, and the mixture was stirred for 1 hour. The mixture was diluted with saturated brine, and the organic phase was separated. The aqueous phase was extracted with ether twice. The combined organic phases were extracted with saturated brine, dried over sodium sulphate, filtered, and evaporated to dryness, leaving 89.4 g of a yellow solid. The solid was dissolved in ether (100 ml), and hexane was added. Boiling and cooling gave a fine white powder (37.68 g, 0.1545 mol, 53%).

VIII.3. 2,2'-bis(2-indenyl)-biphenyl

A 500 ml three-necked flask fitted with a reflux condenser and nitrogen inlet, was charged with 2,2'-biphenylboronic acid (12.2 g, 0677 mmol), and 2-bromoindene (24.38 g, 125 mmol) and potassium carbonate (15.8 g, 0.114 mol). The flask was brought under an atmosphere of dry nitrogen by purging for approx. 1 hour. Then, dimethoxyethane (125 ml) and water (63 ml) were added. The two phase system of two solutions was deoxygenated by consecutively evacuation until reflux and letting nitrogen gas in three times. Palladium-tetrakis(triphenylphosphine) (2.9 g, 2.5 mmol, 5 mol %) was added, and the yellow mixture was heated to reflux. Reflux was continued for a period of 16 hour. After cooling, the mixture was diluted with water and acetone, then the white powder filtered (fraction A, 4.76 g, 12.5 mmol, 18.5%). From the mother liquor another crop of brown powder(fraction B, 4.38 g, 11.5 mmol, 13.1%) could be obtained by dilution with water and partial evaporation of solvent. By crystallization from acetone with some dichloromethane, pure product was obtained. Total yield of pure product: 5.98 g (15.6 mmol, 23.1%).

VIII.4. [2,2'-bis(2-indenyl) biphenyl]zirconiumdichloride

A 100 ml Schlenk flask charged with a stirring bar and 2,2'-bis(2-indenyl)biphenyl (3.84 g, 10.0 mmol) was brought under an atmosphere of dry. Dry ether (40 ml) was added. The resulting suspension was cooled to 0° C. by ice-bath, and a solution of n-butyllithium (1.6 M in hexanes, 12.5 ml, 20.0 mmol) was added. The mixture was allowed to warm to room temperature. slowly. The crystals slowly dissolved, while a fine suspension formed. Stirring at room temperature was continued for 4 hour.

Meanwhile, a suspension of zirconium tetrachloride (2.34 g, 10 mmol) in dry ether (40 ml) was prepared. The suspensions (of dianion in ether and of zirconium tetrachloride in ether) were cooled in an acetone/dry ice bath, and mixed via a bended connection tube. The temperature was allowed to rise to room temperature. After stirring for two days, the suspension was filtered (under nitrogen atmosphere), and the residue washed with dry ether three times (the last washing was colourless). The residue was dissolved partly in boiling toluene (260 ml), and the suspension filtered hot under an atmosphere of dry nitrogen The clear yellow filtrate was cooled slowly to ambient temperature, giving yellow crystals of pure product (3.30 g, 6.08 mmol, 60.6%). The filtrate was used to extract the residue once more (boiling), and cooling to -200C afforded another crop (0.65 g, 1.2 mmol, 12%).

VIII.5. [2,2'-bis(2-indenyl)biphenyl]hafniumdichloride

To a suspension of 2,2'-bis(2-indenyl)biphenyl (1.01 g; 2.64 mmol) in diethylether (50 ml) was added a solution of n-butyllithium in hexanes (1.60 M; 3.30 ml; 5.50 mmol) at room temperature. The resulting red-brown solution was stirred during 4 hours and, after it was cooled to −70° C., a pre-cooled (−70° C.) slurry of HfCl$_4$ (0.85 g; 2.65 mmol) in diethylether (10 ml) was added at once. The temperature was allowed to rise to room temperature and the mixture was stirred for 16 hours. The resulting off-white slurry was filtered and the remaining solid was washed with diethylether twice. The residual solid was extracted with boiling toluene (3 times with 20 ml) and the filtrate was cooled down to room temperature overnight. The yellow crystals were filtered off washed with toluene and dried (1.18 g; 71%)

VIII.6. Supported [2,2'-bis(2-indenyl)biphenyl] zirconiumdichloride

Silica (Grace Davison 2101) was heated at 200° C. under a stream of nitrogen for 6 hours. To 7.3 g of this silica was added 70 ml of toluene. The slurry was stirred and 49.4 ml of a 10 wt-% of methylalumoxane (diluted from a 30 wt % solution in toluene obtained from Albemarle) was added slowly. The resulting slurry was stirred for 16 hours at room temperature (20° C.), after which the solvent was removed by evaporation at 30° C.

To a slurry of 2.1 g of the obtained solid in 30 ml of toluene was added a solution of 24 mg of [2,2'-bis(2-indenyl)biphenyl]-zirconiumdichloride in 20 ml of toluene, and the resulting slurry was stirred overnight. The slurry was then decanted and dried by evaporation at 35° C.

Example IX

The Synthesis of ZrCl$_2$-1-(9-fluorenyl)-2-(2-indenyl)-benzene-complex

IX.1. 1-(9-hydroxyfluorenyl)-2-bromobenzene

A solution of MgBr$_2$ in diethylether was prepared from 69.88 g (372 mmol) 1,2-dibromoethane and 9.04 g (372 mmol) Mg in 500 ml diethylether. This solution was added to a solution of 74.0 g (186 mmol), 2,2-dilithio-1,1-biphenyl-TMEDA adduct in 500 ml diethylether. The solution was stirred for 1 hour. A white suspension of 2,2-diMgBr-1,1-biphenyl was formed. To this solution was added 39.99 g (186 mmol) methyl 2-bromobenzoate and was stirred for 8 hour. To the solution was added 500 ml 5% HCl. The waterphase was washed for three times with diethylether. The organic phase was washed once with water and dried with NaSO$_4$. Diethylether was evaporated. Cristallisation from ligroin gave 50.0 g (147 mmol, 79%) purified product.

IX.2. 1-(9-fluorenyl)-2-bromobenzene

To 20.0 g (59 mmol) 1-(9-hydroxyfluorenyl)-2-bromobenze in a three-necked bottle (1000 ml) was added 14.76 g (369 mmol) CH$_3$CN, 39.1 g (362 mmol) (CH$_3$)$_3$SiCl and 54. 31 g (362 mmol) NaI. After 18 h stirring at RT 50 ml ethanol was added to the mixture. A solution of 200 ml 10% NaHCO$_3$ in water was added, after neutralisation a solution of 200 ml 10% sodiumthiosulphate in water is added. The solution was extracted with diethylether. The waterlayer was washed three times with diethylether. The organic phase was washed once with water. Diethylether was evaporated. The product was purified over silica (ligroin). The product was collected in two fractions, 4. 84 g (14.5 mmol) pure product and 8 g of a mixture of product and biphenyl.

IX.3. 1-(9-fluorenyl)-2-(2-indenyl)-benzene

From the mixture of biphenyl and product was taken 5.22 g. This was dissolved in 60 ml dimethoxyethane and 30 ml water in a threenecked bottle (250 ml). To this solution was added 2.50 g (15.6 mmol) 2-indenylboronic-acid, 2.30 g (16.4 mmol) K$_2$CO$_3$ and 0.63 g (0.55 mmol) Pd(Ph)$_3$P. The mixture was stirred overnight. 10 ml of 10% HCl was added. The crude product was extracted with dichloroethane and the solvent was evaporated. Cristallisation from ethanol gave 2.59 g (7.28 mmol, 89%) pure product.

IX.4. ZrCl$_2$-1-(9-fluorenyl)-2-(2-indenyl)-benzene-complex

To a solution of 1.05 g (3.0 mmol) 1-(9-fluorenyl)-2-(2-indenyl)-benzene in 12 ml diethylether was added 3.8 ml (1.6 mol/l) n-butyllithium in hexanes. After stirring for 4 hours the solution was added to a mixture of 0.699 g (3.0 mmol) ZrCl$_4$ in 12 ml diethylether at −78° C. The mixture was stirred for 18 hour. The solvent was evaporated and the product was washed 3 times with cold ligroin. To the crude product was added active carbon and 40 ml toluene. The mixture was filtrated hot. The remaining solids were washed once more with 40 ml hot toluene. The two fractions crystallize at 20° C. The product was filtrated an dried, 0.30 g (0.58 mmol, 19%) pure product were obtained.

Polymerisation Examples

Examples X–XIX and Experiment A 400 ml of pentamethyl heptane (abbreviation: PMH), ethylene and, eventually, 25 ml 1-octene were supplied to a 1.3-liter reactor, with heating to polymerisation temperature ($T_p$); the pressure was 2 MPa. Next, 0.78 ml (1.6 M solution in toluene) of methylaluminoxane (Witco) and the catalyst solution or slurry (0.125 ml of a 0.001 m solution in toluene) were premixed at room temperature for 1 minute and then supplied to the reactor. The catalyst supply vessel was rinsed out with 100 ml of pentamethylheptane (PMH). The pressure in the reactor was kept constant by supplying ethene. By cooling the reactor the temperature deviation from the setting was limited to a maximum of 50° C. After 10 minutes the polymerisation was stopped and the polymer was worked up by draining the solution and boiling it down under vacuum at 50° C. The results are given in Table I.

Comparative Experiment A

The Synthesis of [1,2-bis(2-indenyl)ethane] zirconium dichloride

A.1. 1,2-bis(2-hydroxy-2-indenyl)ethane

To 3.6 g of magnesium turnings (0.15 mol) was added 20 ml of THF. The magnesium was activated with 0.5 ml of 1,2-dibromoethane. After 15 minutes at room temperature the solvent was removed from the magnesium and 20 ml of THF was added. A solution of 6.0 g of α,α-dichloro-o-xylene (34 mmol) in 325 ml of THF were added dropwise over a period of 4 hours. The mixture was stirred for 16 hours at room temperature. A solution of 2.45 g of dimethyl succinate (17 mmol) in 50 ml of THF was added during 4 hours. After the addition was complete stirring was continued for 1 hour. To the reaction mixture was added 25 ml of water dropwise followed by 100 ml of 10% hydrochloric acid. The THF was evaporated and the residue was extracted with dichloromethane 3 times. The combined organic layers were dried over magnesium sulphate. The magnesium sulphate was filtered off and the filtrate was evaporated to dryness. The product was purified by column chromatography. (eluent: petroleum ether/THF, 3/1, v/v). Yield 2.1g (42%) of a white powder.

A.2. 1,2-bis(2-indenyl)ethane 2.0 g of the diol (6.8 mmol) was dissolved in 50 ml of THF. This solution was added to a mixture of 0.88 g sodiumhydride (37 mmol) and 3.1 g methyl iodide (22 mmol) in 30 ml of THF over a period of 15 minutes. To reaction mixture was stirred for 16 hours at room temperature. While cooling with a water/ice bath 20 ml of water was added carefully. THF was evaporated and the residu was extracted twice with 50 ml of dichloromethane. The combined organic layers were dried over sodiumsulphate. The sodiumsulphate was filtered off and the filtrate was evaporated to dryness to yield 2.0 g of an off white powder. The crude product was suspended in 30 ml of diethylether and while cooling with ice 19.0 ml of n-butyllithium (1.6 M in hexane, 30 mmol) was added dropwise over a period of 15 minutes. The mixture was stirred for 16 hours at room temperature. 25 ml water was added. This resulted in three phases, two liquid layers and a solid. The water layer and the solid were separated from the organic layer. The solid was filtrated from the water layer and washed twice with 10 ml of ethanol and twice with 10 ml of petroleum ether. After drying 1.24 g of the product was obtained. The organic layer and the layers from the washings of the solid were combined, dried over sodium sulphate and filtrated. The filtrate was evaporated to dryness and the solid residu was washed twice with 10 ml of petroleum ether. This afforded another 0.27 g of product. Total yield 1.51 g (86%).

A.3. [1,2-bis(2-indenyl)ethane]zirconium dichloride 1.5 g of 1,2-bis(2-indenyl)ethane (5.8 mmol) was dissolved in 20 ml of THF. The solution was cooled to −30° C. and 7.3 ml of butyllithium (1.6M in hexane, 11.7 mmol) was added dropwise. The temperature was allowed to rise to room temperature and stirring was continued for 4 hours. In a separate Schlenk flank 1.43 g of zirconiumtetrachloride was dissolved in 30 ml of THF at −60° C. The temperature was raised to room temperature and than cooled again to −60° C. The suspension of the di anion was cooled to −60° C. and combined with the zirconium tetrachloride. The reaction mixture was stirred overnight at room temperature. THF was evaporated and the residu was extracted with dichloromethane. The undissolved solids were filtered off and the filtrate was freed from solvent. The residue was washed twice with petroleum ether (25 ml) and dried in vacuo. Yield 1.4 g of a yellow powder (58%).

TABLE I

| Example | Catalyst | $T_p$ (° C.) | CY (kg PE/gM. 5 min.) | Mw (*1000) | mol % C8 |
|---|---|---|---|---|---|
| X | Example III.5 | 180 | 412 | 5.9 | |
| | | 150 | 1109 | 7.3 | |
| XI | Example II.12 | 150 | 2244 | | |
| | | 120 | 6129 | | |
| | | 100 | 8927 | 4.0 | |
| | | 100 | 13259 | | 1.44 |

TABLE I-continued

| Example | Catalyst | $T_p$ (° C.) | CY (kg PE/gM. 5 min.) | Mw (*1000) | mol % C8 |
|---|---|---|---|---|---|
| XII | Example IV.2 | 150 | 1736 | | |
| | | 120 | 6222 | | |
| | | 100 | 8055 | 4.5 | |
| | | 100 | 5990 | | 2.35 |
| XIII | Example III.5 | 90 | 33344 | | |
| | | 100 | 31397 | 6.4 | |
| | | 100 | 24793 | | 2.8 |
| XIV | Example III.6 | 100 | 305 | 47 | |
| | | 120 | 169 | | |
| | | 150 | 138 | | |
| | | 100 | 314 | | 2.3 |
| XV | Example V.2 | 100 | 991 | | |
| | | 120 | 1682 | 420 | |
| | | 150 | 617 | | |
| | | 120 | 1327 | | 5.3 |
| XVI | Example VII.2 | 100 | 478 | | |
| | | 120 | 2243 | 590 | |
| | | 120 | 1766 | | 2.5 |
| XVII | Example VI.2 | 100 | 210 | | |
| | | 120 | 475 | 390 | |
| | | 120 | 324 | | 5.92 |
| XVIII | Example VIII.4 | 100 | 11840 | 340 | |
| | | 120 | 4473 | 215 | |
| | | 150 | 1166 | | |
| | | 160 | 1030 | 59 | |
| | | | 2294 | | 3.0 |
| XIX | Example IX.4 | 100 | 66500 | 70 | |
| | | 120 | 32690 | | |
| | | 150 | 8380 | | |
| | | 100 | 38630 | | 1.5 |
| Exp. A | Example A.3 | 150 | 1513 | | |
| | | 120 | 1853 | | |

Example XX

In a 2.0 l. steel autoclave, $4.10^{-4}$ mol tributylaluminium as scavenger was introduced with 1000 ml. pentamethylheptane (PMH). Ethylene was then added to the reactor to obtain a pressure of 2 MPa. 48 mg of supported catalyst according to example VIII.6 was brought in a syringe and slurried with 10 ml petroleumether. This slurry was transferred into the injection vessel that was connected to the autoclave. When the autoclave was brought to the polymerisation temperature (90° C.), the catalyst slurry was injected into the reactor and the polymerisation starts under constant ethylene pressure. After 30 minutes of polymerisation, the ethylene was vented off and the polymer was collected and dried in a vacuum oven at 70° C. 110 g. polymer was obtained with a good morphology.

Examples XXI–XXXIII 300 ml of dried heptane or pentamethylheptane and half of the prescribed amount of methylaluminoxane (MAO) (6 ml of a 10 wt. % solution in toluene (Witco)) were supplied to a 2-liter stainless steel autoclave, while heating to polymerisation temperature. The reaction content was continuously flushed with dried nitrogen and the pressure was 0.24 MPa. Consequently, the metallocene catalyst (5 μmol) and the second half of the MAO amount were premixed for at least 1 minute at room temperature as a solution or slurry in 75 ml toluene and then supplied to the reactor. The catalyst supply vessel was rinsed out with 225 ml of heptane. The pressure in the reactor was dropped to 0.1 MPa and propylene was supplied to the reactor until a constant pressure of 0.6 MPa was obtained. A constant stirring speed of 1000 rpm was maintained during the polymerisation. By cooling the reactor, the temperature deviation from the setting was limited to a maximum of 2° C. After 30 minutes, the polymerisation was stopped, the propene was vented and the obtained polymer was worked up by drying the solution under air and eventually under vacuum at 60° C. The results are given in Table II.

TABLE 2

| Example | catalyst | $T_p$ (° C.) | Activity (kg PP/g cat $h^{-1}$) | mmmm % ($^{13}$C-NMR) | mis-insertions (2, 1- + 1, 3- insertions) [d] |
|---|---|---|---|---|---|
| XXI | example III.5 | 80 | 9,3 | | |
| XXII [a] | example I.6 | 110 | 7,9 | | |
| XXIII | example II.12 | 80 | 9,9 | | |
| XXIV | example VIII.4 | 40 | 3,6 | | |
| XXV [b] | example VIII.5 | 80 | 4,4 | | |
| XXVI [a] | example VII.2 | 110 | 8,9 | | |
| XXVII [a] | example VI.2 | 110 | 7,1 | | |
| XXVIII [e] | example IX.4 | 50 | 74 | | |
| XXIX [c] [f] | example IX.4 [c] | 80 | 76 | | |
| XXX | example VIII.4 | 40 | 21,5 | 91,6 | 2,8 |
| XXXI | example VIII.4 | 80 | 3,0 | 78,7 | 3,2 |
| XXXII | example VIII.5 | 40 | 2,6 | 95,1 | 1,3 |
| XXXIII | example VIII.5 | 80 | 15,6 | 91,5 | 2,2 |

What is claimed is:

1. Indenyl compound of formula (1)

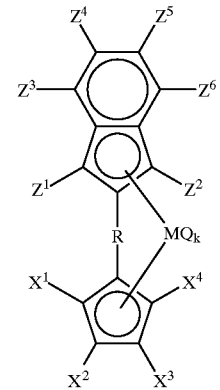

wherein:

M is a transition metal from the lanthanides or from group 3, 4, 5 or 6 of the Periodic System of Elements, Q is an anionic ligand to M, k is the number of Q groups and is equal to the valence of M minus 2, R is a bridging group and Z and X are substituents, characterised in that R contains at least one sp2-hybridised carbon atom that is bonded to the indenyl group at the 2-position with the exclusion of Ti(deshydronorbiphenacene) dichloride.

2. Indenyl compound of formula (2)

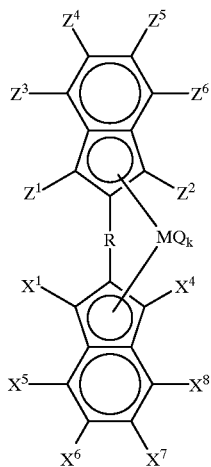

wherein:
M is a transition metal from the lanthanides or from group 3, 4, 5 or 6 of the Periodic System of Elements,
Q is an anionic ligand to M,
k is the number of Q groups and is equal to the valence of M minus 2,
R is a bridging group
and Z and X are substituents, wherein R contains at least one sp2-hybridised carbon atom that is bonded to one of the indenyl groups at the 2-position with the exclusion of Ti(deshydronorbiphenacene)dichloride.

3. Indenyl compound according to claim 1, wherein R contains at least one aryl group.

4. Indenyl compound according to claim 1 wherein R contains at least one phenylene group.

5. Indenyl compound according to claim 1 wherein R contains a bisaryl group.

6. Indenyl compound according to claim 1 wherein R is a 2,2'-biphenylene.

7. Indenyl compound according to claim 1 wherein M is Ti, Zr or Hf.

8. Indenyl compound according to claim 1 wherein Q is Cl or a methyl group.

9. Ligand precursor of formula (3)

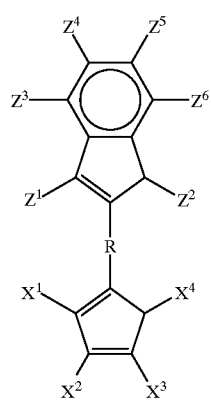

wherein:
R is a bridging group
and Z and X are substituents, wherein R contains at least one sp2-hybridised carbon atom that is bonded to the indene group at the 2-position with the exclusion of 2,2'-bis(2-1H-indenyl)-6,6'-dimethyl-1,1'-biphenyl, 2,2'-bis(2-1H-indenyl)-1,1'-biphenyl and 2,2'-bis(2-1H-indenyl)-1,1'-binaphthalene.

10. Ligand precursor of formula (4)

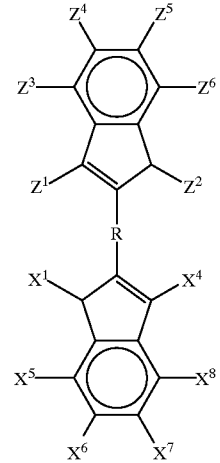

wherein:
R is a bridging group
and Z and X are substituents wherein R contains at least one sp2-hybridised carbon atom that is bonded to one of the indene groups at the 2-position with the exclusion of 2,2'-bis(2-1H-indenyl)-6,6'-dimethyl-1,1'-biphenyl, 2,2'-bis(2-1H-indenyl)-1,1'-biphenyl and 2,2'-bis(2-1H-indenyl)-1,1'-binaphthalene.

11. Ligand precursor according to claim 9 wherein R contains at least one phenylene group.

12. Ligand precursor according to claim 9, wherein R is a 2,2'-biphenylene with the exclusion of a ligand with the structure 2,2'-bis(2-1H-indenyl)-1,1'-biphenyl.

13. Process for the preparation of a ligand precursor of formula (3) by a cross-coupling reaction of two 2-indenyl precursors of formula (5) with a bridging precursor $R(Y^2)_2$

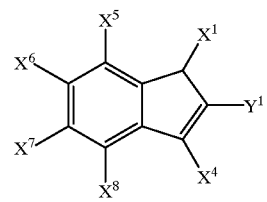

(5)

wherein:
$X^1$ to $X^8$: are substituents,
$Y^1$ and $Y^2$ are either a leaving group or a metal containing group,
R is a bridging group, comprising the steps of reacting 2 equivalents of the 2-indenyl precursors with 1 equivalent of the bridging precursor, $Y^2$ being a leaving group in the case that $Y^1$ is a metal containing group and $Y^2$ being a metal containing group in the case that $Y^1$ is a leaving group.

14. Process for the preparation of a ligand precursor of formula (4) by a cross-coupling reaction of one 2-indenyl precursor of formula (5) with one cyclopentadienyl precursor of formula (6) with a bridging precursor $R(Y^2)_2$:

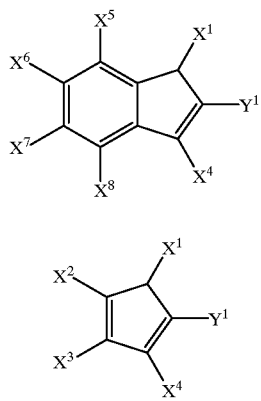

(5)

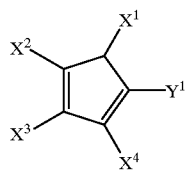

(6)

wherein:

X¹ to X⁸: are substituents,

Y¹ and Y² are either a leaving group or a metal containing group,

R is a bridging group, comprising the step of reacting 1 equivalent of the 2-indenyl precursor and 1 equivalent of the cyclopentadienyl precursor with 1 equivalent of the bridging precursor, Y² being a leaving group in the case that Y¹ is a metal containing group and Y² being a metal containing group in the case that Y¹ is a leaving group.

15. Process for the preparation of a ligand precursor according to claim 13, wherein one of the leaving groups Y1 or Y2 is boronic acid.

16. Process according to claim 15, wherein the other leaving group is bromine.

17. Process according to claim 14, wherein the indenyl-2-boronic acid and the boronic acid substituted cyclopentadienyl precursor are prepared by contacting of an indene substituted with a halogen on the 2-position respectively of an cyclopentadiene containing compound, substituted with a halogen, with magnesium to form a Grignard solution which reacts with a trialkylborate.

18. Process for the polymerisation of an olefin, in which an indenyl compound, optionally in the presence of a cocatalyst, is contacted with an olefin, wherein the indenyl compound is an indenyl compound according to claim 1.

19. Process according to claim 18, wherein the catalyst and/or the cocatalyst are supported on a carrier material.

20. Process according to claim 19, wherein the carrier material is silica.

21. Process according to claim 20, wherein the olefin is an α-olefin.

22. Process according to claim 21, wherein the olefin is chosen from the group comprising ethylene, propylene, butene, pentene, hexene, heptene, octene or mixtures thereof.

23. Process according to claim 18, wherein a polymer is prepared on the basis of ethylene and/or propylene.

24. Process according to claim 23, wherein a rubbery polymer is prepared on the basis of ethylene, propylene and, optionally, a diene.

* * * * *